(12) United States Patent
Broadley et al.

(10) Patent No.: US 7,862,800 B1
(45) Date of Patent: Jan. 4, 2011

(54) RADIOPAQUE CYANOACRYLATE COMPOSITIONS

(75) Inventors: Kenneth N. Broadley, Naas (IE); Noeleen B. Swords, Dublin (IE); Clare P. Grealis, Dublin (IE)

(73) Assignee: Henkel AG & Co. KGaA, Duesseldorf (DE)

( * ) Notice: Subject to any disclaimer, the term of this patent is extended or adjusted under 35 U.S.C. 154(b) by 1396 days.

(21) Appl. No.: 11/328,109

(22) Filed: Jan. 10, 2006

Related U.S. Application Data

(60) Provisional application No. 60/643,604, filed on Jan. 14, 2005.

(51) Int. Cl.
*A61K 49/04* (2006.01)
*A61K 31/74* (2006.01)
*A61K 31/785* (2006.01)
*A61K 31/765* (2006.01)
*A01N 41/02* (2006.01)
*A61M 31/00* (2006.01)

(52) U.S. Cl. .............. 424/9.455; 424/9.4; 424/9.45; 424/78.31; 424/78.35; 424/78.37; 514/527; 604/48

(58) Field of Classification Search ............ 424/9.4, 424/9.45, 9.455, 78.31, 78.35, 78.37; 514/527; 604/48
See application file for complete search history.

(56) References Cited

U.S. PATENT DOCUMENTS

| | | | | |
|---|---|---|---|---|
| 4,359,454 A | * | 11/1982 | Hoffman | 424/9.451 |
| 4,713,235 A | | 12/1987 | Krall | 424/5 |
| 5,342,716 A | * | 8/1994 | Kato et al. | 430/91 |
| 5,530,037 A | | 6/1996 | McDonnell | 522/79 |
| 5,695,480 A | | 12/1997 | Evans | 604/264 |
| 5,874,044 A | | 2/1999 | Kotzev | 422/40 |
| 6,040,408 A | | 3/2000 | Koole | 526/292.1 |
| 6,136,236 A | | 10/2000 | Boccard | 264/40 |
| 6,310,166 B1 | | 10/2001 | Hickey | 526/348.2 |
| 6,428,800 B2 | | 8/2002 | Greenspan | 424/405 |
| 6,562,317 B2 | | 5/2003 | Greff | 424/1.25 |
| 6,579,916 B1 | | 6/2003 | Askill | 522/152 |
| 6,759,028 B2 | | 7/2004 | Wallace | 424/1.25 |

FOREIGN PATENT DOCUMENTS

| | | |
|---|---|---|
| EP | 0684222 | 10/1998 |
| EP | 0659441 | 3/2002 |
| WO | WO 2005.053578 | 6/2005 |

OTHER PUBLICATIONS

Artola et al., "A Radiopaque Polymeric Matrix for Acrylic Bone Cement", J. Biomaterial. Res. Part B; Appl. Biomaterial, 64B, 44-55 (2002).
Kruft et al., "Studies on Two New Radiopaque Polymeric Biomaterials", J. Biomed. Mat'ls Res., 28, 1259-66 (1994).

* cited by examiner

*Primary Examiner*—Michael G Hartley
*Assistant Examiner*—Leah Schlientz
(74) *Attorney, Agent, or Firm*—James E. Piotrowski; Steven C. Bauman

(57) ABSTRACT

This invention relates to sterilized cyanoacrylate adhesive compositions with x-ray imagining capabilities, methods of making such compositions, and methods of using such compositions.

8 Claims, No Drawings

RADIOPAQUE CYANOACRYLATE COMPOSITIONS

This application claims the benefit of an earlier filing date from U.S. Provisional Application No. 60/643,604, filed Jan. 14, 2005.

BACKGROUND OF THE INVENTION

1. Field of the Invention

This invention relates to sterilized cyanoacrylate adhesive compositions with x-ray imaging capabilities, methods of making such compositions, and methods of using such compositions.

2. Brief Description of Related Technology

In recent years, the use of cyanoacrylate-based biomedical adhesives and sealants has increased dramatically. Once seen as a triage type of treatment, cyanoacrylate-based biomedical adhesives and sealants have found their way into more mainstream use, for instance, as topical wound closure treatments. More recently, internal applications of cyanoacrylate-based biomedical adhesives and sealants have been and are currently being explored.

In such applications, it is desirable for the cyanoacrylate-based biomedical adhesives and sealants to be sterilized against bacterial growth. One commercially successful way to achieve that sterilizing is described and claimed in U.S. Pat. No. 5,530,037 (McDonnell). The '037 patent, under which a product manufactured by Henkel Loctite (Ireland) Ltd. and distributed in the U.S. by Tyco Healthcare under the registered trade mark INDERMIL, provides a curable cyanoacrylate adhesive composition for use in bonding tissue, where the composition has been sterilized in liquid form by gamma irradiation and is the irradiation product of a composition comprising a cyanoacrylate monomer; and a combination of an anionic stabilizer and a free-radical stabilizer in amounts effective to stabilize the composition during irradiation and to stabilize the sterilized composition during storage prior to cure.

Particularly for internal use applications in patients, it would be desirable to observe the location of the cyanoacrylate-based biomedical adhesive and sealant after dispensing onto or into the desired area of the patient. With certain cyanoacrylate-based biomedical adhesives and sealants designed and developed for topical use, a dye has been introduced into the adhesive or sealant composition to assist in visualization on the skin once applied. See for instance HISTOACRYL BLUE from B. Braun Melsungen AG. However, with internal applications, a simple dye cannot be visualized. Instead, a radiopaque material should be employed.

Radiopaque materials have been proposed for use with cyanoacrylates in the past. For instance, U.S. Pat. No. 4,713,235 (Krall) describes and claims radiopaque polymerizable cyanoacrylate compositions that are mixtures of an ester of 2-cyanoacrylic acid and a radiopaque additive stable to and not substantially decreasing the storage life of the cyanoacrylate ester. This additive the '235 patent reports is selected from triiodophenol, iodoform and tetraiodoethylene. The so-formed radiopaque polymerizable cyanoacrylate compositions have between 0.5 and 11 mole percent iodine atoms. These iodo additives have poor solubility in cyanoacrylates generally, however, and thus require heating in order to dissolve them.

Other contrast agents have been used in cyanoacrylates as well. For instance, U.S. Pat. No. 6,562,317 (Greff) describes and claims a composition suitable for treating a solid mass tumor in a mammal. This composition includes a biocompatible prepolymer; an optional biocompatible solvent; and from about 0.1 to about 25 weight percent of a water insoluble radioisotope having from a radioactive content of from about 0.5 microcurie to about 100 millicurie. The biocompatible prepolymer may be cyanoacrylate. Optionally, the composition may include a non-radioactive contrast agent, which may be water soluble or water insoluble. The water-soluble contrast agents are selected from metrizamide, iopamidol, iothalamate sodium, iodomide sodium, and meglumine; the water-insoluble contrast agents are selected from tantalum, tantalum oxide, barium sulfate, tungsten, gold and platinum.

And U.S. Pat. No. 6,759,028 (Wallace) describes and claims a method for treating an arteriovenous malformation ("AVM") in a mammal. This method includes the steps of selecting a fluidic composition comprising a biocompatible prepolymer, a water insoluble radioisotope and optionally a biocompatible solvent; and injecting a sufficient amount of the composition into one of more vascular sites leading to or within the AVM under conditions, where a solid mass is formed thereby ablating at least part of the then AVM, where the radioisotope is employed in an amount effective to further ablate the AVM and to inhibit regrowth of the AVM. Like the '317 patent above, the composition may be a cyanoacrylate with a contrast agent selected from those recited in the preceding paragraph. U.S. Pat. No. 5,695,480 (Evans) speaks more generally about specific compositions embraced by those used in the methods of the '317 and '028 patents. Water insoluble contrast agents are undesirable because they tend to destabilize cyanoacrylates (causing the cyanoacrylates to prematurely cure) and sediment from the cyanoacrylate composition. Once sedimented, at least with silver contrast agents in thickened cyanoacrylate compositions, the silver contrast agents are difficult to re-disperse.

Also, in the context of treating AVMs, butyl cyanoacrylate has been combined with Lipiodol (iodinized ethyl esters of poppy seed oil fatty acids) and tantalum. However, Liopodol destabilizes the butyl cyanoacrylate, and as such the components must be mixed immediately prior to use. Thus, such Lipiodol/tantulum-containing cyanoacrylate compositions do not have a shelf life, and cannot reasonably be made to be a practical commercial product in a one part composition.

In A. Artola et al., "A Radiopaque Polymeric Matrix for Acrylic Bone Cement", *J. Biomaterial Res. Part B; Appl. Biomaterial* 64B, 44-55 (2002), the authors refer to the use of a radiopaque agent, 4-iodophenol methacrylate, in a bone cement for implants that consisted of methyl methacrylate as the resin matrix. In their conclusions, the authors note that cements containing 15% 4-iodophenol methacrylate performed better as a bone cement than conventional cements containing barium sulfate as an x-ray contrast agent.

Despite the state of the technology, there has been no disclosure, teaching, suggestion or motivation to date to use 4-iodophenol methacrylate (or any iodophenol-substituted methacrylate) in a matrix other than methacrylates for use as anything other than bone cements. Thus, because of the state of the technology, there was no disclosure, teaching, suggestion or motivation to date to use iodophenol-substituted methacrylates in a cyanoacrylate composition, let alone one that has been sterilized and whose end use is suitable for use as adhesives and sealants with soft tissue.

SUMMARY OF THE INVENTION

The present invention thus provides a shelf stable, one-part cyanoacrylate adhesive composition having as a radiopaque agent, iodo-substituted phenol (meth)acrylates. The composition should be sterilized, and when sterilized is in liquid form prior to exposure to sterilization conditions and remains flowable at room temperature even after sterilization.

The iodo-substituted phenol (meth)acrylates may be embraced by H$_2$C=C(X)—COOY, where X is hydrogen or alkyl and Y is Z$_m$—Ar—I$_n$; Z is alkyl, halogen (other than iodine), hydroxyl and carboxyl, m is 0 or 1, and n is 1-5, provided that when m is 0, n is 1-5 and when m is 1, n is 1-4.

The invention also provides a method of making such a cyanoacrylate adhesive composition; and methods of using such a cyanoacrylate adhesive composition, such as to bond soft tissue or adheringly seal a vascular cavity.

DETAILED DESCRIPTION OF THE INVENTION

As noted above, the invention provides a shelf stable, one-part cyanoacrylate adhesive composition having in addition to a cyanoacrylate component, iodo-substituted phenol methacrylates as a radiopaque agent.

The iodo-substituted phenol methacrylates may be embraced by H$_2$C=C(X)—COOY, where X is hydrogen or alkyl and Y is Z$_m$—Ar—I$_n$; Z is alkyl, halogen (other than iodine), hydroxyl and carboxyl, m is 0 or 1, and n is 1-5, provided that when m is 0, n is 1-5 and when m is 1, n is 1-4.

The iodophenol methacrylate in a more particular embodiment may be embraced by

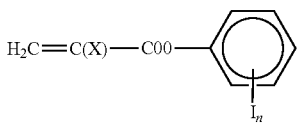

wherein X is hydrogen or methyl and n is 1-5. For instance, a particularly desirable iodophenol methacrylate is

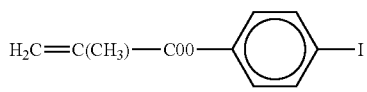

Di or tri-iodo substituted phenol methacrylates are also desirable, as less of the radiopaque agent can be used in the composition to achieve a comparable visualization effect under x-ray exposure.

Other desirable iodophenol methacrylates include

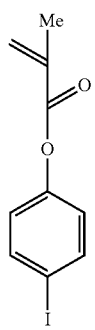

A

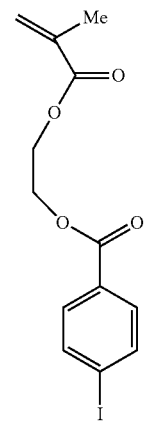

B

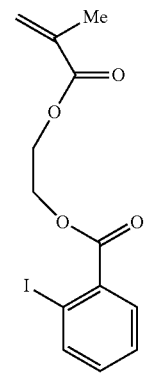

C

In addition, iodonized-phenol derivatives of polymethyl methacrylates may also be used. When used, these materials are capable of serving a dual function—one as a radiopaque agent and the other as a thickener.

The radiopaque agent should be included in an amount in the range of 0.5 to 75 percent by weight, desirably 5-50 percent by weight, such as 7 to 20 percent by weight. The radiopaque agent should be added to the cyanoacrylate before sterilization, and the composition should not require further additives once it is to be sterilized.

The cyanoacrylate component includes cyanoacrylate monomers which may be chosen with a raft of substituents, such as those represented by H$_2$C=C(CN)—COOR, where R is selected from C$_{1-15}$ alkyl, alkoxyalkyl, cycloalkyl, alkenyl, aralkyl, aryl, allyl and haloalkyl groups. Desirably, the cyanoacrylate monomer is selected from methyl cyanoacrylate, ethyl-2-cyanoacrylate, propyl cyanoacrylates, butyl cyanoacrylates, octyl cyanoacrylates, allyl-2-cyanoacrylate, 8-methoxyethyl-2-cyanoacrylate and combinations thereof. A particularly desirable cyanoacrylate monomer for use herein is n-butyl cyanoacrylate.

As is known in the art of manufacturing cyanoacrylates, stabilizers are included to decrease the potential of premature polymerization and hence enhance shelf life stability. To that end, since basic materials react quickly with cyanoacrylates at even trace levels, an acidic material is added to neutralize any such basic contaminants. In addition, free radical stabilizers in the form of anti-oxidants are included as are anionic stabilizers. Such acidic, free radical and anionic stabilizers are well known in the cyanoacrylate art and may be found described in the '037 patent.

In the context of irradiated cyanoacrylate compositions, the '037 patent teaches a combination of anionic and free radical stabilizers to maintain a flowable cyanoacrylate even after exposure to sterilizing doses of gamma irradiation. The technology of the '037 patent may also be employed herein, and as such is expressly incorporated herein by reference. See also U.S. Pat. No. 6,310,166.

In addition or alternatively, other sterilization methods may be used. For instance, U.S. Pat. No. 5,874,044 (Kotzev) speaks to a method of sterilizing a 2-cyanoacrylate preparation that consists of only a 2-cyanoacrylate compound and one or more anionic or free-radical polymerization inhibitors that prevent premature polymerization. The method includes the step of heating the preparation in a suitable container that is hermetically closed to a temperature of at least 160° C. without causing polymerization of the 2-cyanoacrylate preparation. Related U.S. Pat. No. 6,136,236 speaks to package comprising a sealed aluminum container and a composition so sterilized the above method heat treatment disposed therein.

Also, E-beam sterilization may be used in the practice of the present invention. For instance, U.S. Pat. No. 6,248,800 speaks to a method for preparing a polymerizable, sterile, cyanoacrylate ester composition in a shipping element comprising multiple individual package cyanoacrylate compositions. The method includes the steps of (a) selecting a packaging element; (b) adding a cyanoacrylate ester composition comprising a polymerizable cyanoacrylate ester to an individual packaging element selected in (a) above; and (c) combining multiple individual package elements into a shipping element; (d) exposing the shipping element formed in (c) above to a sufficient dosage of E-beam irradiation maintained at an initial fluence of at least 2 µCurie/cm$^2$ to sterilize both the packaging elements and the cyanoacrylate ester composition without gelling the composition. Significantly, the average bulk density of the materials comprising the shipping element is less than about 0.2 gm/cm$^3$.

In U.S. Pat. No. 6,579,916 a method is disclosed for preparing a polymerizable, sterile, cyanoacrylate ester composition through the exposure to a predetermined dosage of visible light irradiation having wavelengths of from 390 to 780 nanometers which predetermined dosage is sufficient to sterilize the polymerizable cyanoacrylate ester composition without gelling the polymerizable cyanoacrylate ester composition and is from about 0.01 to 50 J/cm$^2$.

And ultrafiltration sterilization may be used too.

In order to sterilize by way of exposure to gamma-irradiation, the inventive cyanoacrylate compositions are packed into a suitable container, such as a bottle, tube, or vial. The filled bottles are then sealed in metal foil (e.g., aluminium foil) pouches and subjected to gamma irradiation, such as with a dose of 25 kGy under ambient conditions. Irradiation doses of less than 25 kGy should suffice as well, such as doses as low as 10 kGy.

Free radical stabilizers and anionic stabilizers are frequently added to cyanoacrylates either during or after manufacture to assist in providing a meaningful commercial shelf life.

Free radical stabilizers or anti-oxidants which may be used include methyl hydroquinone, catechol, tert-butyl hydroquinone, 4-tert-butoxyphenol, 4-ethoxyphenol, 3-methoxyphenol, 2-tert-butyl-4-methoxyphenol, 2,2-methylene-bis-(4-methyl-6-tert-butylphenol), butyl hydroxy toluenes (such as BHT, or 4-methyl-2,6-di-tert-butylphenol) and butylated hydroxy anisole (BHA).

Concentrations of the free radical stabilizer may vary in the range of 500 to 10,000 ppm. However, the appropriate concentration can be determined by testing along the lines described in the '037 patent.

Known anionic (or acid) stabilizers for cyanoacrylate adhesives include sulphur dioxide ($SO_2$), sulphonic acids, sulphuric acid, sulphur trioxide, phosphorous acids, carboxylic acids, picric acid, boron trifluoride ($BF_3$), $BF_3$-ether complexes, $BF_3.2H_2O$, citric acid, hydrofluoric acid, tin (IV) chloride, iron (III) chloride, and combinations thereof.

$SO_2$ is particularly well known as a satisfactory stabilizer for cyanoacrylate adhesives under normal conditions of storage and use, and during sterilization, such as gamma irradiation treatment. Concentrations of anionic stabilizers in cyanoacrylate compositions ordinarily vary in the range of 25 to 500 ppm. From an $SO_2$ standpoint, sterilization of cyanoacrylate compositions of this invention can be achieved using this anionic stabilizer in the range 20 to 150 ppm.

In the invention compositions, initial results of stabilization with $BF_3.2H_2O$ have shown at least as promising stability data as with $SO_2$.

Conventional additives such as thickeners, dyes and thixotropic agents may be included in the compositions as required. However, for medical or veterinary use care must be taken as noted in the '037 patent to ensure that additives do not introduce toxic contaminants which survive or are produced by irradiation. Sterilization by way of irradiation may itself cause some thickening of the composition. For medical or veterinary use a maximum composition viscosity after sterilization of about 200 mPas is desirable, preferably less than 50 mPas, especially less than 25 mPas, unless of course a thickened version is desired.

The invention will be more fully appreciated by a reading of the following examples.

EXAMPLES

Example 1

Adapted from M. Kruft et al., "Studies On Two New Radiopaque Polymeric Biomaterials", *J. Biomed. Mat'ls Res.*, Vol. 28, 1259-1266 (1994), 4-iodophenol methacrylate was prepared as follows:

1. 15.05 grams of 4-iodophenol and 13.85 grams of dry triethylamine were added to 200 ml dry dichloromethane in a round bottom flask and cooled with a cooling bath of ethanol and liquid nitrogen to a temperature of −5° C.

2. 8.55 g of methacryoyl chloride in 75 ml of dry dichloromethane was added dropwise at a temperature of −5° C. with constant stirring to the solution of iodophenol/triethylamine. This addition was carried out over a period of 60 minutes. After completion of the addition, the cooling bath was removed and the mixture was allowed to stir for 4 to 6 hours. After 6 hours of stirring the mixture was cooled to −5° C., and then 250 ml of distilled $H_2O$ was added.

3. The organic phase was separated and washed with saturated $NaHCO_3$ (200 ml×3 washes), $H_2O$ (200 ml×1 wash), and brine (200 ml×3 washes).

4. The organic layer was dried over $MgSO_4$ overnight, and then filtered and concentrated to yield a yellow/orange oil.

5. The yellow/orange oil was purified by column chromatography to yield a white solid. $^1$H-NMR characterization of the 4-iodophenol methacrylate product showed: δ 2.02 (3H, t), δ 5.73 (1H, hept), δ 6.31 (1H, hept), δ 6.87 (2H, sext), and δ 7.65 (2H, sext).

Example 2

The 4-iodophenol methacrylate prepared above in Example 1 was used to formulate cyanoacrylate compositions.

Thus, n-butyl cyanoacrylate (with 5,000 ppm BHA and 60 ppm $BF_3$) was used as the cyanoacrylate component, to which was added with mixing at room temperature 10% by weight 4-iodophenol methacrylate.

Example 3

The radiopaque cyanoacrylate composition of Example 2 was sterilized by gamma irradiation through exposure to a dose of 25-30 kGys.

Example 4

As comparative examples, n-butyl cyanoacrylate, n-butyl cyanoacrylate with 10% 4-iodophenol and n-butyl cyanoacrylate with 10% triiodophenol were prepared. These samples were used as formulated and subjected to sterilization by exposure to gamma irradiation, in the same manner as Example 3.

The stability and viscosity measurements of 4-iodophenol and 2,4,6-triiodophenol in n-butyl cyanoacrylate ("n-bu CA") at various concentrations are shown below in Tables 1 and 2:

TABLE 1

| Sample (in n-bu CA) | Stability | | | |
|---|---|---|---|---|
| | Days @ 82° C. pre | Days @ 82° C. post | Days @ 55° C. pre | Days @ 55° C. post |
| 1% 4-iodophenol | 28-29 | 7-8 | >69 | >43 |
| 5% 4-iodophenol | 27-28 | 7-8 | >69 | >43 |
| 10% 4-iodophenol | 27-28 | 7-8 | >69 | >43 |
| 15% 4-iodophenol | 23-24 | 7-8 | >69 | >43 |
| 20% 4-iodophenol | 23-24 | 7-8 | 53-54 | 39-40 |
| 1% 2,4,6-triiodophenol | 21-22 | 7-8 | >69 | >43 |
| 2.5% 2,4,6-triiodophenol | 2-4 | 1-2 | 17-19 | 14-15 |
| 5% 2,4,6-triiodophenol | −1.5 | <1 | 9-10 | 3 |

Of note are the following observations relating to stability:
No more than 5% 2,4,6-triiodophenol will dissolve in n-bu CA, a 10% mixture (suspension) will gel after <1 month at 4° C.
2,4,6-triiodophenol destabilizes n-bu CA even at low concentrations
4-iodophenol is less destabilizing to n-bu CA

TABLE 2

| Sample (in n-bu CA) | Viscosity | | |
|---|---|---|---|
| | Pre Viscosity (mPas) | Post Viscosity (mPas) | Viscosity Increase (%) |
| 5% 4-iodophenol | 2.82 | 4.44 | 57 |
| 10% 4-iodophenol | 3.06 | 5.32 | 74 |
| 2.5% 2,4,6-triiodophenol | 2.76 | 4.89 | 77 |
| 5% 2,4,6-triiodophenol | 2.97 | 7.91 | 166 |

Of note is the following observation relating to viscosity: larger increases seen post gamma for triiodophenol in CA Example 5

As a comparative evaluation of pre and post-irradiation viscosity increase, n-butyl cyanoacrylate (with 5,000 ppm, BHA and 60 ppm $BF_3$), and radiopaque cyanoacrylate compositions with 10% 4-iodophenol methacrylate in the n-butyl cyanoacrylate were prepared and viscosity measurements taken with a Paar Physica MCR300 viscometer. Viscosity measurements made on the Paar Physica MCR300 viscometer before and after exposure to 25 to 30 kGy gamma irradiation are shown below in Table 3:

TABLE 3

| Sample | Viscosity | | |
|---|---|---|---|
| | Pre Viscosity (mPas) | Post Viscosity (mPas) | Viscosity Increase (%) |
| 4-iodophenol methacrylate ("4IM") | 5.40 | 5.98 | 10.74 |
| n-bu CA (5,000 ppm BHA, 60 $BF_3$) | 2.72 | 16.30 | 500 |
| 10% 4IM mixed with n-bu CA | 2.90 | 9.14 | 215 |

Example 6

The fixture times using acylonitrite-butadiene-styrene copolymer test specimens for the n-butyl cyanoacrylate and the radiopaque cyanoacrylate composition range from a low of 20 seconds for the n-butyl cyanoacrylate to a high of 35 seconds for the radiopaque cyanoacrylate composition.

While an increase of fixture time of up to about nearly 100% was observed, in real time the increase is not commercially significant.

The bond strengths on these test specimens range from 1.673 to 7.094 $N/mm^2$. The presence of the radiopaque agent did not appreciably affect the bond strength values observed.

Example 7

Radiopaque cyanoacrylate compositions were prepared as described above, with the concentration of 4-iodophenol methacrylate ranging from 5% to 50% at intervals of 5%, 10%, 20% and 50%. The so-prepared compositions were dispensed onto an X-ray film and allowed to cure.

The X-ray film was then exposed to X-ray and developed. The resulting film showed each of the compositions as a white streak, with the compositions having the highest concentration of radiopaque agent showing the most brilliance on the X-ray film.

What is claimed is:

1. A shelf-stable, one-part cyanoacrylate composition, wherein the composition has been sterilized in liquid form and remains in liquid form after sterilization, wherein the composition comprises:
   a) a cyanoacrylate monomer; and
   b) a radiopaque agent having the following structure $H_2C=C(X)-COOY$, wherein X is hydrogen or alkyl and Y is $Z_n-Ar-I_n$; wherein Z is alkyl, Ar is substituted with a carboxyl linker when m is 1, m is 0 or 1, and n is 1-5.

2. A composition according to claim 1 further comprising a combination of an anionic stabilizer and a free-radical stabilizer in amounts effective to stabilize the composition during sterilization and to stabilize the sterilized composition during storage prior to cure.

3. A composition as in claim 1, wherein the composition is exposed to a dose of gamma irradiation that is in the range of 10-35 kGy.

4. A composition according to claim 1 wherein the cyanoacrylate monomer has the following structure $H_2C=C(CN)-COOR$, wherein R is a member selected from the group consisting of $C_{1-15}$ alkyl, alkoxyalkyl, cycloalkyl, alkenyl, aralkyl, aryl, allyl and haloalkyl groups.

5. A composition according to claim 1 wherein the radiopaque agent has the following structure

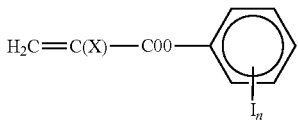

wherein X is hydrogen or methyl and n is 1-5.

6. A composition according to claim 1 wherein the radiopaque agent has the following structure

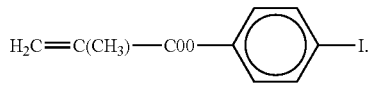

7. A composition according to claim 1 wherein the radiopaque agent has the following structure

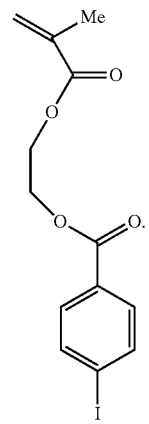

8. A composition according to claim 1 wherein the radiopaque agent has the following structure

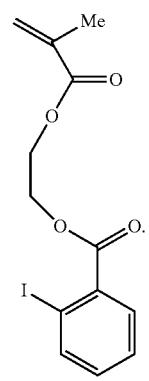

* * * * *